United States Patent [19]

Roe et al.

[11] Patent Number: 5,256,419
[45] Date of Patent: Oct. 26, 1993

[54] BIOLOGICAL & DUST CONTROL METHODS FOR BULK/GRANULAR SOLIDS

[75] Inventors: Donald C. Roe, Tabernacle, N.J.; Dwight P. Davis, Holland; Kevin C. Manning, Richboro; Edmund J. Bockowski, Furlong, all of Pa.; Marc Verschoren, Ramsel, Belgium

[73] Assignee: Betz Laboratories, Inc., Trevose, Pa.

[21] Appl. No.: 23,465

[22] Filed: Feb. 25, 1993

Related U.S. Application Data

[63] Continuation of Ser. No. 848,783, Mar. 10, 1992, abandoned, which is a continuation of Ser. No. 733,075, Jul. 17, 1991, abandoned, which is a continuation of Ser. No. 451,385, Dec. 15, 1989, abandoned.

[51] Int. Cl.⁵ .............................................. A01N 25/24
[52] U.S. Cl. ...................................... 424/407; 252/88; 252/106; 424/405; 514/514; 514/515; 504/116
[58] Field of Search .................. 71/67; 252/88, 106; 424/405, 407; 514/514, 515

[56] References Cited

U.S. PATENT DOCUMENTS

| | | | |
|---|---|---|---|
| 865,578 | 9/1907 | Ellis | 252/88 |
| 3,563,461 | 2/1971 | Cole, Jr. | 239/9 |
| 3,891,571 | 6/1975 | Lambou et al. | 252/354 |
| 4,136,050 | 1/1979 | Brehm | 252/88 |
| 4,400,220 | 8/1983 | Cole, Jr. | 134/18 |
| 4,428,984 | 1/1984 | Shimizu et al. | 427/220 |
| 4,551,261 | 11/1985 | Salihar | 252/88 |
| 4,569,989 | 2/1986 | Madison | 424/78.37 |
| 4,610,311 | 9/1986 | Bronner et al. | 169/45 |
| 4,780,233 | 10/1988 | Roe | 252/88 |
| 4,795,590 | 1/1989 | Kent et al. | 252/307 |
| 4,795,764 | 1/1989 | Alm et al. | 521/107 |
| 4,847,067 | 7/1989 | Thomas | 424/639 |
| 4,857,209 | 8/1989 | Lyons et al. | 210/755 |
| 4,869,905 | 9/1989 | Sobek et al. | 426/406 |
| 4,946,311 | 8/1990 | Rosar et al. | 405/129 |
| 5,019,564 | 5/1991 | Lowe et al. | 514/75 |

FOREIGN PATENT DOCUMENTS 1106907A  8/1984  U.S.S.R.

*Primary Examiner*—Thurman K. Page
*Assistant Examiner*—Robert H. Harrison
*Attorney, Agent, or Firm*—Alexander D. Ricci; Steven D. Boyd

[57] ABSTRACT

A foam carrier for a dust control agent and a pesticidal material is provided to control fugitive dust dissemination and biological activity in bulk/granular solids.

4 Claims, No Drawings

BIOLOGICAL & DUST CONTROL METHODS FOR BULK/GRANULAR SOLIDS

This is a continuation of copending application Ser. No. 07/848,783 filed on Mar. 10, 1992, now abandoned which is a continuation of Ser. No. 07/733,075 filed Jul. 17, 1991, now abandoned which in turn is a continuation of Ser. No. 07/451,385 filed Dec. 15, 1989, now abandoned.

FIELD OF THE INVENTION

The present invention relates to methods of controlling dust and biological activity in bulk/granular solids.

BACKGROUND OF THE INVENTION

Dust dissemination poses safety, health and environmental problems in many commercial environments. For example, dust suppression is of particular concern in the coal mining industry where coal dust dissemination caused by wind or transit motion may lead to black lung disease if inhaled over lengthy periods of time. Ignition of small dust particles is also a concern. Similar concerns exist when other materials such as sulfur, phosphates, clays or other finely divided ores and minerals generate dust in handling operations, during mining, transportation, storage or use.

In addition to the mining industry, many other commercial activities also provide the potential for dust control problems. For instance, fertilizer dust has raised health concerns due to human and animal inhalation and also poses the problems of ignition or explosion. The cement industry also is concerned with fugitive dust dissemination during manufacture, transport and storage operations.

Industrial sources of fugitive dust include open operations, leaks and spills, storage, disposal, transit and/or poor housekeeping where sundry finely divided solid particulates are involved. In noncommercial settings, dust generation may pose health and safety problems, as with the fertilizer use, as well as housekeeping or aesthetic problems.

In combination with the concerns and problems involved with the manufacture, storage and handling of items inclined to the formation of fugitive dust, concerns related to biological organisms also exist with respect to these items. For example, the production of acidic leachate i.e., acid mine drainage, found in coal and coal refuse piles is related to biological activity in the piles. Surfactant based biocides have been known to reduce the population of bacteria responsible and thereby inhibit acid mine drainage. Dried sewage sludge which can be used as fertilizer or mixed with coal for use as a fuel exhibits both dust generation problems and odor caused by biological action. Similarly, grain and animal feed which exhibit well known problems with respect to dust generation could be beneficially treated with biological agents to control insect or rodent damage or spoilage.

Thus, in numerous areas where dry, bulk or granular solids are manufactured, stored and handled the combination of dust generation and biological activity are of concern. Thomas, U.S. Pat. No. 4,847,067 discloses the treatment of grain or hay to control the moisture induced growth of mold. The treatment also provides dust control. The described treatment comprises an aqueous solution of one or more salts of propionic acid and a deliquescent material and preferably also a humectant. The aqueous treatment is sprayed onto the grain or hay.

The use of foams as dust control agents is known in the coal mining industry. For example, Cole U.S. Pat. No. 4,400,220 discloses the use of foam of a specific small bubble size to control dust in coal mining operations at the working face and at transfer points. Roe, U.S. Pat. No. 4,780,233 discloses a water insoluble elastomeric polymer and oil combination which may be applied in a foam carrier to inhibit dust dissemination. Ellis, U.S. Pat. No. 865,578 discloses a non-foam dust control agent for application to a road surface.

Other, agricultural uses for foams are known such as for freeze control. For example, Cole, U.S. Pat. No. 3,563,461 discloses a system of applying foam to agricultural plants to inhibit freeze damage. Lambou et al., U.S. Pat. No. 3,891,571 discloses a foam containing whey solids for use as frost and freeze protection for plants. The foam of Lambou et al. can be used as a carrier for the surface application of agricultural chemicals such as herbicides, fungicides, etc.

SUMMARY OF THE INVENTION

The present invention is directed to a foam carrier for a dust control agent which also includes a pesticidal material. The combination of a pesticidal agent or agents in a foam dust control composition has been found to be particularly effective when dealing with bulk or granular solids. The foam dust control agent of the present invention may include binders which function as dust control extenders to provide residual dust control. The foam may be composed of anionic, nonionic and/or cationic surfactants in aqueous solutions foamed in a conventional manner. The pesticidal material may be composed of a water and/or oil based biocide, fungicide, or other pesticide.

The present invention has been found to be effective at applying a dust control and a pesticidal material to bulk solids. The combination of the present invention may be applied during a transfer operation to control dust dissemination and biological activity such as odor, acid mine drainage and insect or pest damage. The use of a foam to apply the dust control agents and pesticidal agents provides maximum distribution of the minimal effective amount of active ingredients thereby minimizing costs as well as required treatment concentrations.

DETAILED DESCRIPTION OF THE PREFERRED EMBODIMENTS

The present invention provides a method of inhibiting dust generation and biological activity in bulk solid materials. The method of the present invention may employ the application of a so called "one drum treatment". The treatment is composed of a foam which includes dust control agents and pesticidal agents. The bulk solids which are treated by the present invention include materials which tend to generate dust during manufacture, storage and handling and which also are desirably treated for control of biological activity. Examples include dried sludge, coal, animal feed, grain and absorbants such as cat litter. The dust and pesticidal agents are applied as a foam which can be intimately mixed with the material to be treated. The use of foam as a distribution medium allows effective application of the control agents to bulk solids. The control agents of the present invention are thereby applied to essentially the entire surface of the bulk solid as opposed to surface treatments such as spraying a coal pile.

The foam of the present invention may be composed of anionic, nonionic and/or cationic surfactants in aqueous solutions. The generation of the foam may be by any suitable means such as described in U.S. Pat. No. 4,400,220, Cole, the contents of which are hereby incorporated by reference. The use of such foams will provide dust control most effectively when applied during manufacturing and transfer operations. Exemplary Surfactant Foaming Agents include alkyl aryl sulfonate, alkyl ether sulfate, alpha olefin sulfonate, alpha sulfo methyl ester, alkyl sulfosuccinate, alkanolamide, amine oxide, and betaines. For effective dust control during storage, water and/or oil based binders such as mineral or vegetable oils, elastomeric and water soluble polymers and lignosulfonate compositions may be desirable. Such binders or extenders provide more effective residual dust control.

The pesticidal agent(s) portion of the present invention may include water and/or oil based biocides, fungicides, and pesticides. The use of such pesticidal agents in combination with a foam dust control agent provides for effective distribution over the surface area of the bulk solid. Further, the application of a pesticidal agent in a foam allows extremely efficient distribution of a relatively small amount of active material. For example, in typical prior art grain or animal feed treatment, large volumes of relatively concentrated gaseous fumigants are employed to distribute the fungicide throughout the mass of the grain. In the method of the present invention, because essentially all of the biological control agent ends up on the surface of the bulk solid, rather than escaping to the atmosphere, lower volumes and concentrations of treatment material may be employed.

Exemplary pesticidal agents include, but are not limited to, n-alkyl dimethyl benzyl ammonium chloride (and other quaternary ammonium biocides), dodecyl guanidine hydrochloride, acrolein (produced in situ from suitable precursors), methylene bisthiocyanate, bis trichloromethyl sulfone, bromo-nitrostyrene, 2,2-dibromo-3-nitrilopropionamide,5-chloro-2-methyl-4-isothiazolin-3-one (with 2-methyl-4-isothiazolin-3-one), 2-bromo-2-nitro-propane-1,3-diol, and decyl thioethyl amine, either alone or in combination. The combination of a formulation containing methylene bisthiocyanate and bromo-nitrostyrene (Slimicide C-41) and an oil based binder (Betz DG-1259F) emulsified in water with a surfactant foaming agent (FlowPro®1105) has been found to provide effective dust control as well as odor control when applied as a foam to a coal/sludge mixture. The commercial products (Slimicide C-41, Betz DG-1259F, and FlowPro 1105) are available from Betz Laboratories, Inc., Trevose, PA. Such coal/sludge mixtures are kiln dried and employed as inexpensive fuels in cement plants or similar applications.

The application of a fungicide to grain in an aqueous dust control foam would be effective at inhibiting the formation and dissemination of grain dust. Further, such a combination would provide effective control of insect damage. The highly efficient application of a fungicide such as acrolein generated in situ from a suitable precursor, see U.S. Pat. No. 4,851,583 Bockowski et al in a foam would provide effective control at reduced active treatment levels.

The invention will now be further described with reference to a number of specific examples which are to be regarded solely as illustrative and not as restricting the scope of the invention.

EXAMPLES

A sludge/coal mixture was dried in a kiln and treated with a foamed emulsion comprising:

0.12% C14–C16 alpha olefin sulfonate sodium salt
0.11% alkyl ether sulfate sodium salt
1.98% naphthonic process oil
0.001% polyisobutylene
0.05% Betz® Slimicide C-41

An untreated sludge/coal mixture exhibited a high level of dust generation and a strong odor and visible biological activity believed to be fungus or mold. The sludge/-coal mixture treated with foamed emulsion exhibited a very low level of dust generation and no odor or visible evidence of biological activity. Betz® Slimicide C-41 is a broad spectrum biocide available from Betz Laboratories Inc., of Trevose, PA. The active biocidal agents are beta-bromo-beta nitrostyrene (BNS) at 9.2% and methylene bis thiocyanate (MBT) at 4.9%. (See U.S. Pat. No. 4,579,665, Davis et al and U.S. Pat. No. 3,898,343, Swered et al). All percentages are in weight percent.

The combination of the present invention would be similarly effective at inhibiting the formation of biologically induced acid waste, such as acidic leachate called acid mine drainage. When coal or coal refuse is stored in piles, aqueous drainage or leachate often is acidic. The acidic nature of the leachate is related to biological activity within the coal pile. Similar acidic waste can be found in other ore and mineral piles. Surfactant based biocides such as alkyl benzene sulfonates, and alkyl sulfates sprayed onto the coal piles have been shown to reduce the bacteria and inhibit the acid mine drainage. Dust dissemination is also a problem in such coal storage piles. The application of foam dust control agent(s) with a pesticidal control agent(s) and a binder during formation of such piles would provide effective dust control and inhibit biological activity throughout the pile, not just at the surface.

Grains and animal feed are often treated with mineral oil and/or water for dust control in a separate application from fumigation. Typically, post harvest pesticides such as methyl chloride, aluminum phosphide, or certain organophosphates are employed for fumigation. The application of a foam dust control agent which includes a dust control extender and a post harvest pesticide during handling of the grain will provide more effective control than prior art treatments. The method of the present invention will effectively control grain dust as well as insect damage. In the treatment of grains and animal feed, it is desirable to limit the moisture content of the foam to avoid the undesirable addition of moisture to the material.

While this invention has been described with respect to particular embodiments thereof, it is apparent that numerous other forms and modifications of this invention will be obvious to those skilled in the art. The selection of appropriate surfactants, foam extenders and biological control agents is primarily dependent upon the bulk solids to be treated and compatibility of the components. The appended claims and this invention generally should be construed to cover all such obvious forms and modifications which are within the true spirit and scope of the present invention.

What is claimed is:

1. A method of reducing the dissemination of fugitive dust particles into the atmosphere from a bulk solid by applying a foam dust control agent to said bulk solid wherein said foam dust control agent consists of more than about 0.2% anionic, nonionic and/or cationic surfactant as foaming agent and a biocidally effective amount of a biocide consisting of a combination of methylene bisthiocyanate and bromo-nitrostyrene in a ratio of about 2 to 1.

2. The method of claim 1 wherein said foam dust control agent includes a binder in an amount sufficient to provide residual dust control.

3. A method of reducing the dissemination of fugitive dust particles and applying a biocidal control agent to a bulk solid consisting of applying a foamed aqueous anionic, nonionic and/or cationic surfactant solution, including a combination of methylene bisthiocyanate and bromo-nitrostyrene in a ratio of about 2 to 1 as a biocidal control agent.

4. The method of claim 3 wherein said foam dust control agent includes a binder in an amount sufficient to provide residual dust control.

* * * * *

UNITED STATES PATENT AND TRADEMARK OFFICE
CERTIFICATE OF CORRECTION

PATENT NO. : 5,256,419

DATED : Oct. 26, 1993

INVENTOR(S) : Donald C. Roe, et al.

It is certified that error appears in the above-identified patent and that said Letters Patent is hereby corrected as shown below:

On the title page, Item [75] Inventors should read as follows:

[75] Inventors: Donald C. Roe, Tabernacle, N.J.; Marc Verschoren, Ramsel, Belgium Signed and Sealed this Twenty-first Day of June, 1994

Attest:

BRUCE LEHMAN

Attesting Officer  Commissioner of Patents and Trademarks